(12) United States Patent
Luloh et al.

(10) Patent No.: US 8,608,753 B2
(45) Date of Patent: *Dec. 17, 2013

(54) RETRACTABLE TIP FOR VITRECTOMY TOOL

(75) Inventors: K. Peter Luloh, Stuart, FL (US); Tarek Shawky Hassan, Ann Arbor, MI (US); Michael Annen, Ft. Pierce, FL (US)

(73) Assignee: Insight Instruments, Inc., Stuart, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/542,817

(22) Filed: Jul. 6, 2012

(65) Prior Publication Data
US 2012/0283741 A1    Nov. 8, 2012

Related U.S. Application Data

(63) Continuation of application No. 12/472,549, filed on May 27, 2009, now Pat. No. 8,216,246, which is a continuation-in-part of application No. 11/463,465, filed on Aug. 9, 2006, now Pat. No. 7,549,972.

(60) Provisional application No. 61/101,454, filed on Sep. 30, 2008.

(51) Int. Cl.
*A61F 9/007* (2006.01)

(52) U.S. Cl.
USPC .......................................................... 606/107

(58) Field of Classification Search
USPC ............. 606/107, 167, 170, 180; 604/22, 44, 604/164.1–164.12, 167.01, 170.01, 170.02
See application file for complete search history.

(56) References Cited

U.S. PATENT DOCUMENTS

| 1,087,845 | A | 2/1914  | Stevens          |
| 4,108,182 | A | 8/1978  | Hartman et al.   |
| 4,368,734 | A | 1/1983  | Banko            |
| 4,475,904 | A | 10/1984 | Wang             |
| 4,530,356 | A | 7/1985  | Helfgott et al.  |
| 4,674,502 | A | 6/1987  | Imonti           |
| 4,696,298 | A | 9/1987  | Higgins et al.   |
| 4,729,763 | A | 3/1988  | Henrie           |
| 5,047,008 | A | 9/1991  | de Juan, Jr. et al. |
| 5,106,364 | A | 4/1992  | Hayafuji et al.  |
| 5,549,564 | A | 8/1996  | Yoon             |
| 5,716,363 | A | 2/1998  | Josephberg       |

(Continued)

FOREIGN PATENT DOCUMENTS

WO    WO 03/022336    3/2003

*Primary Examiner* — Elizabeth Houston
(74) *Attorney, Agent, or Firm* — Christine Q. McLeod; Beusse Wolter Sanks Mora & Maire, PA

(57) ABSTRACT

A probe for a vitrectomy tool is provided having a vitreous cutter tube having a blunt tip at a distal end and adapted to be coupled at a proximal end to a handpiece of a vitrectomy tool; a retractable outer trocar tube surrounding the vitreous cutter tube having an open distal end with a sharpened edge; and a retraction mechanism coupled to a proximal end of the outer trocar for selectively extending and retracting the outer trocar tube between a first extended position wherein the sharpened edge of the outer trocar is extended beyond the blunt tip of the vitreous cutter tube to facilitate insertion into the eye and a second retracted position wherein the sharpened edge of the outer trocar is retracted behind the blunt tip of the vitreous cutter tube to facilitate safe operation of the probe.

18 Claims, 5 Drawing Sheets

(56) References Cited

U.S. PATENT DOCUMENTS

| | | | |
|---|---|---|---|
| 5,843,111 A | 12/1998 | Vijfvinkel | |
| 5,893,862 A | 4/1999 | Pratt et al. | |
| 5,989,262 A | 11/1999 | Josephberg | |
| 6,059,792 A | 5/2000 | Josephberg | |
| 6,258,111 B1 | 7/2001 | Ross et al. | |
| 6,979,317 B2 * | 12/2005 | Galt et al. | 604/158 |
| 7,419,496 B2 | 9/2008 | Staudner | |
| 2003/0032927 A1 | 2/2003 | Halseth et al. | |
| 2003/0109894 A1 | 6/2003 | Blanco | |
| 2005/0234390 A1 | 10/2005 | Buckman et al. | |
| 2010/0106054 A1 | 4/2010 | Hangai et al. | |

* cited by examiner

RETRACTABLE TIP FOR VITRECTOMY TOOL

CROSS-REFERENCE TO RELATED APPLICATIONS

This application is a continuation of and claims priority to U.S. patent application Ser. No. 12/472,549, filed May 27, 2009, now U.S. Pat. No. 8,216,246 which is a continuation-in-part of and claims priority to U.S. patent application Ser. No. 11/463,465, filed Aug. 9, 2006, now U.S. Pat. No. 7,549,972, which claims priority from U.S. provisional application Ser. No. 61/101,454, filed Sep. 30, 2008, the disclosures of which are all incorporated herein by reference in their entirety.

FIELD OF THE INVENTION

The present invention relates to a retractable tip for a vitrectomy tool, and more particularly to a retractable sharpened tip for use in vitreous cutter probes to provide a sharp tip necessary to insert the probe into the vitreous cavity and, when retracted provides safe operation.

BACKGROUND OF THE INVENTION

It is common practice to extract small amounts of vitreous material from a person's eye in order to provide a sample of the material for examination or in order to remove material so that antibiotics or other drugs may be injected into the eye. Typically, any injection into the eye can result in excess pressure being generated and cause damage to the eye. Accordingly, it is desirable that a volume of vitreous material be removed from the eye prior to injecting an equal volume of drugs into the eyeball.

Various instruments have been developed for this purpose, most of which have been relatively complicated requiring large amounts of supporting equipment. U.S. Pat. No. 6,059,792 describes a sutureless vitrectomy tool that can be used to perform a vitrectomy procedure including removing all of the vitreous material from an eye. However, this device requires an operating room environment and electrical connections to a hand held instrument that utilizes a linear motor to repetitively drive a cutting tool within a 23 gauge stainless steel needle for removing vitreous from the eye. U.S. Pat. Nos. 5,989,262 and 5,716,363 describe sutureless pars plana vitrectomy tools using electrically powered actuators.

SUMMARY OF THE INVENTION

The present invention comprises a unitary mechanical combination injector and vitrector in the form of a manually operable hand tool that can be used when it is only necessary to remove a small volume of vitreous material from the eye ("vitrectomy") in order to provide room for injection of antibiotics or other drugs into the eye. For example, the hand tool may be used to inject an antibiotic into a patient's eye by first removing sufficient vitreous material to approximate the volume of antibiotic fluid so as to prevent an undesirable increase in intraocular pressure. Using the hand tool of the present invention, a drug may be injected into a patient's eyeball in a procedure that may be performed in a doctor's office rather than having to be in a sterile environment of an operating room. Further, the present invention may be designed as a disposable item that is used once and then discarded, thus preventing cross-contamination from multiple use between different patients.

All patents, patent applications, provisional applications, and publications referred to or cited herein, or from which a claim for benefit of priority has been made, are incorporated herein by reference in their entirety to the extent they are not inconsistent with the explicit teachings of this specification.

BRIEF DESCRIPTION OF THE DRAWINGS

A more complete appreciation of the invention and many of the attendant advantages thereof will be readily obtained as the same become better understood by reference to the following detailed description when considered in light of the following drawings, wherein:

FIG. 1A is an enlarged sectional view of a portion of the device of FIG. 1;

Figure 1:
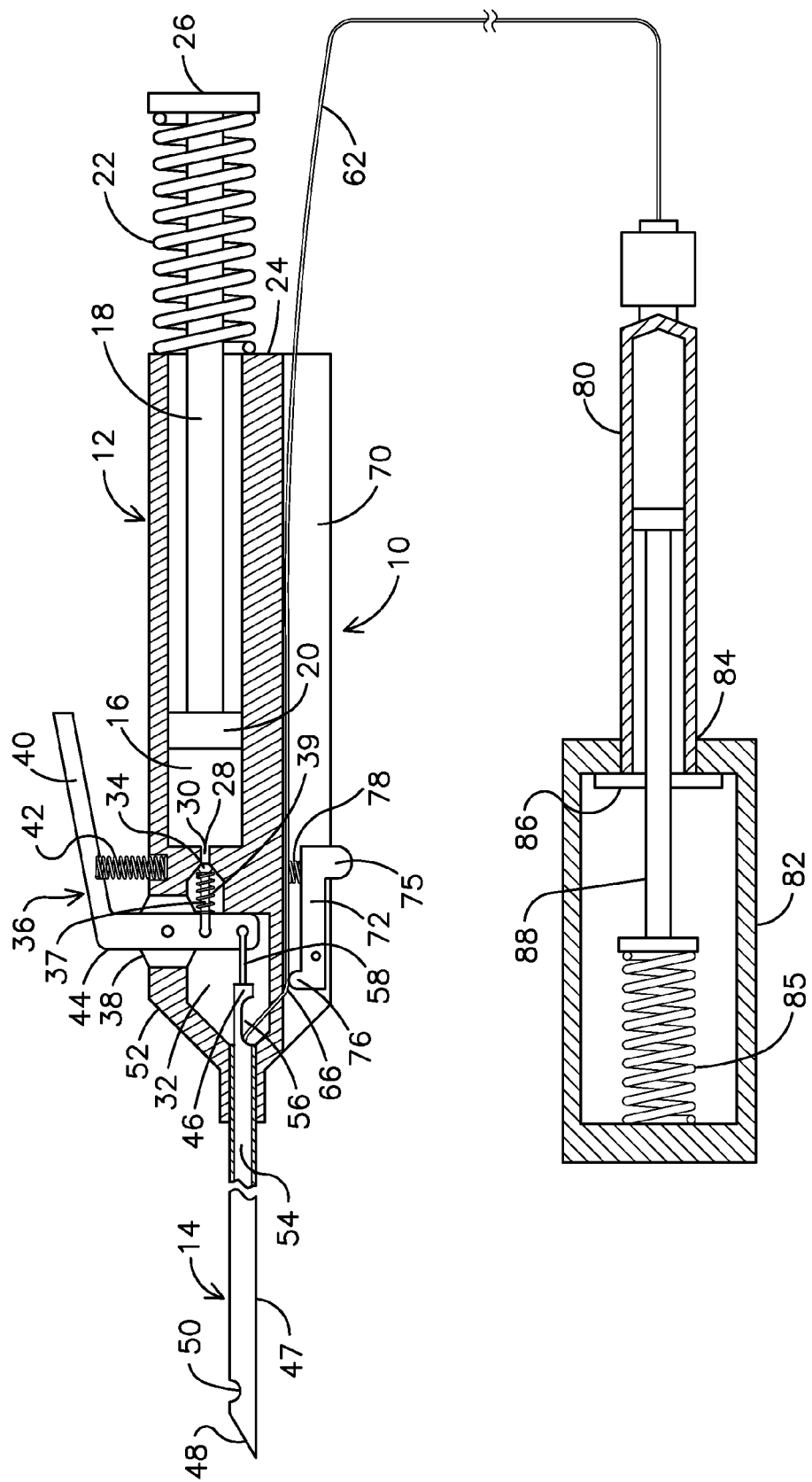
FIG. 1 is a cross-sectional drawing taken along a longitudinal axis of one form of the present inventive injector-vitrector device.

While the present invention will be described with reference to the details of the embodiments of the invention shown in the drawing, these details are not intended to limit the scope of the invention.

DETAILED DESCRIPTION OF THE INVENTION

Referring to the drawings in general and in particular to FIG. 1 and the enlarged section of FIG. 1 shown in FIG. 1A, there is shown one embodiment of the present invention in a form of a manually operated hand tool 10. The tool 10 includes a housing body or body portion 12 and a needle portion 14. The body portion 12 includes several cavities, the largest of which is a vacuum, i.e., a negative pressure, or aspiration cavity 16. A plunger 18 is situated in the cavity 16 and includes a plunger end 20 that sealingly engages the inner surfaces of the body 12 defining the cavity 16. The plunger end 20 may be an elastomeric material or provided with an elastomeric seal such as an O-ring. A spring 22 is positioned about the plunger and reacts between an end 24 of the housing 12 and a cap 26 on the plunger.

At the inner end 28 of cavity 16 there is an orifice 30 that provides an opening into a second cavity 32. The orifice 30 is sealed by a plug 34 attached to a lever 36 via an elongate arm 37 that is held in an extended position by a spring 39. The arm 37 is captured at end 41 in a slot 43 formed in lever 36. The lever 36 is seated in a ball pivot 38 that allows the lever to be pivoted without disrupting the integrity of the cavity 32. The lever 36 has an outer arm 40 that is held in the position shown in FIG. 1 by the action of a spring 42. The spring 42 reacts between the body 12 and an underside of the arm portion 40 to pivot the lever 36 in a direction to maintain the plug 34 seated in the orifice 30. Spring 42 is seated in aperture 45 formed in body 12.

The lever 36 is essentially an L-shaped member in which the outer arm portion 40 is arranged at an obtuse angle with respect to the other arm portion 44. The plug 34 is attached to the arm portion 44 via arm 37. When the arm portion 40 is pressed down causing the lever 36 to pivot, the arm portion 44 moves in a clockwise direction thereby pulling the plug 34 out of the orifice 30 allowing transfer of material between cavity 32 and cavity 16.

Also coupled to the arm portion 44 via connecting rod 58 is a second elongated member 46 (an inner cutter) that extends from an end of the arm portion 44 outward through a central bore of the needle portion 14. The needle portion 14 includes an outer needle 47 and the inner cutter 46. The needle 47, in addition to having a sharpened end 48 to facilitate insertion into the eye, is also provided with an aperture or cut out 50 into which vitreous material will flow when the needle portion 14 is inserted into an eye. As can be seen in FIGS. 1 and 1A, the housing body 12 includes an end portion 52 that engages and holds the outer needle 47 in fixed relationship to the body 12. It can also be seen that the elongated member 46 comprises a hollow tube that fits within the needle 47 and also has a side opening 56 within housing body 12. The connecting rod 58 connects the hollow tube member 46 to the arm portion 44. Accordingly, when the lever 36 is pressed downward, not only does the plug 34 retract from the orifice 30 but also the tube member 46 is driven forward through the needle 47 so that the distal edge 60 of the tube member 46 severs any material protruding into the opening or aperture 50. The action of the inner tube within the needle is more clearly shown in FIGS. 2A and 2B.

Figure 2:
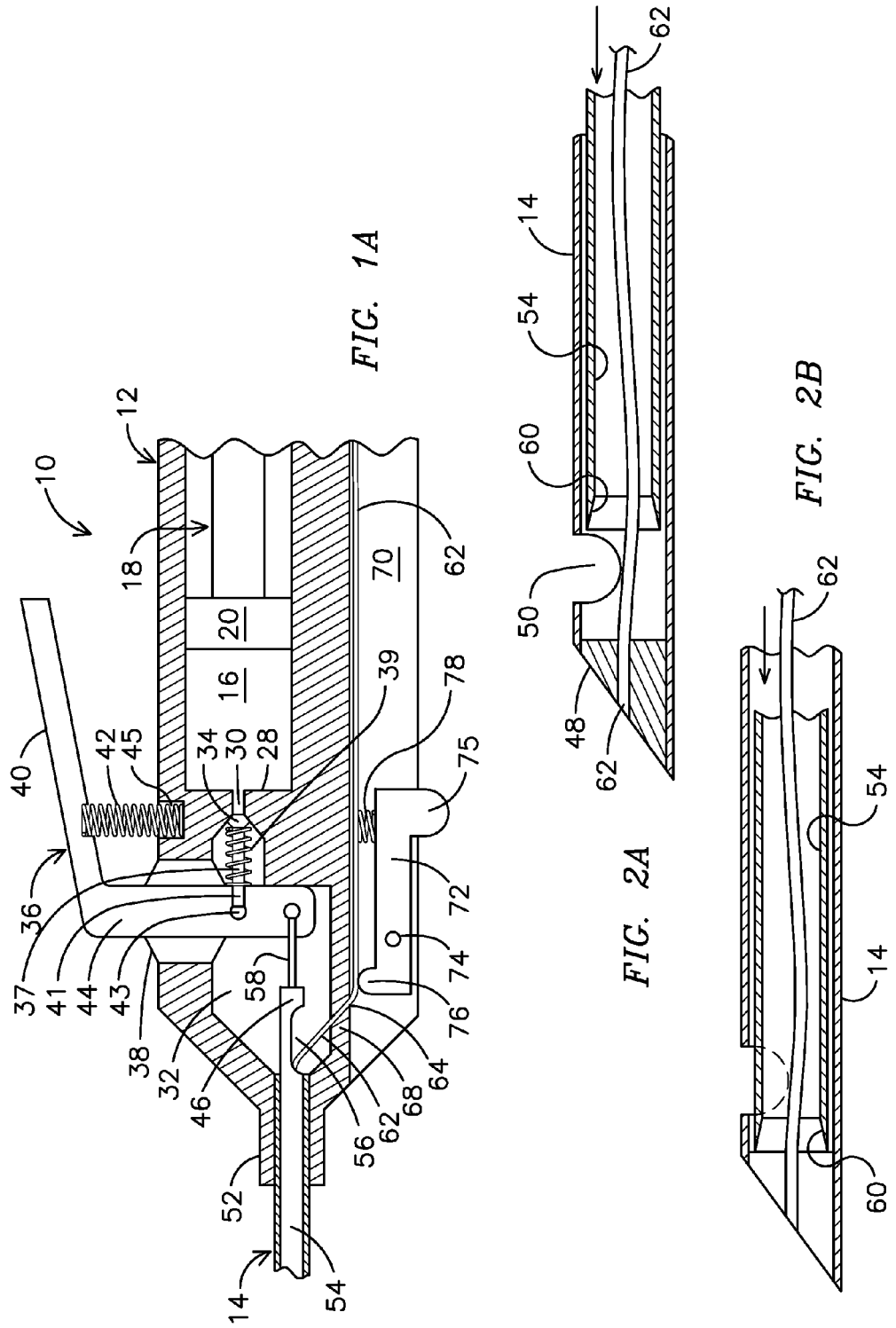
FIGS. 2A and 2B are cross-sectional views of the needle portion of the device of FIG. 1 showing two positions of the inner cutter.

FIGS. 2A and 2B show an enlargement of the needle portion 14 of FIG. 1. It can be seen that the inner tube 46 fits snugly within the inner opening through needle 47. The end of the tube 46 is formed with a sharpened edge at 60 so that when the inner cutting tube member 46 is pressed forward past the aperture 50, member 46 acts as a reciprocal cutter with the sharpened edge cutting off any material protruding into the aperture 50 and causing the cut material to drop into the cavity formed within the inner tube member 46. FIG. 2B illustrates the position of the inner tube member 46 as it has been urged forward past the aperture 50. In FIGS. 2A and 2B, it will also be seen that there is another smaller diameter tube 62 extending through the inner tube 54 and out to the end of the needle portion 14. The tube 62 is used to transport liquid such as antibiotics or drugs or even water into the eye to replace the vitreous material that is removed by the cutting action of the needle and inner tube 54. While the needle portion 14 has been described in what is believed to be a preferred embodiment, it will be recognized that other forms of cutters may be used in the invention. See, for example, cutter descriptions in U.S. Pat. No. 5,716,363. The only requirement is to be able to puncture the eye to excise a portion of the vitreous material and introduce that material into a tube through which it can be removed from the eye by suction. Accordingly, the term "needle portion" is intended to include all such cutters having this capability.

Turning back to FIG. 1, the inner tube 62 exits the tube 54 through the opening 56 and then passes through another opening at 64 in wall 68 of cavity 32. The opening 64 and tube 62 are sized to create a generally leak free connection through the wall 68. The tube 62 then proceeds through a longitudinal opening 70 and extends out the rear end of the body 12. The path of the tube 62 is guided through the passage 70 so that it passes under a second lever 72. The lever 72 has a pivot point at 74 and an inwardly extending arm or protrusion 76 positioned to engage the tube 62. The lever arm 76 is held in contact with the tube 62 by means of a spring 78 pushing on the lever 72 so as to cause a clockwise-directed force on the lever. The spring 78 and lever 72 are sized and arranged so that there is sufficient force exerted on tube 62 to collapse the tube and prevent fluid flow therethrough. The pressure on the tube 62 can be released by pressing downward on lever arm 75 against action of the spring 78 to cause the lever to pivot sufficiently to release enough pressure on the tube so that a flow of fluid can be forced through the tube.

The tube 62 extends outward from the hand tool 10 and connects to a mechanical pressurization system comprising a conventional syringe 80 and a spring-loaded mechanism 82. The syringe 80 is typically supplied with a needle tip (not shown) that is then inserted into a drug container in a conventional manner and a measured amount of drug is drawn into the syringe. In this application, the needle is then removed from the end of the syringe and the tube 62 connected to the syringe in its place. The syringe is then coupled to the spring actuator 82 by simply depressing the spring and inserting the upper part of the syringe into the slot 84 so that the top end 86 of the syringe rests on an inner surface around the slot 84. The spring is then released to press against the plunger 88 of the syringe. The spring 90 pressing against the plunger 18 maintains a fixed pressure of fluid in the tubing 62. As would be recognized, the syringe would be actuated initially to force fluid from the syringe through the tubing 62 until some amount of fluid is released at the end of the tubing at the sharpened end 48 of the needle 14. The lever 72 would then be released to clamp the tubing before inserting the needle 14 into an eye of a patient.

The system of FIG. 1 requires that the plunger 18 be depressed into the cavity 16 before inserting the needle 14 into an eye. Pressing the plunger downward will cause the plug 34 to open slightly at orifice 30 so that the air will be expelled out of the needle 14. However, the sealing action of the plug 34 will prevent air from leaking from the cavity 32 back into the cavity 16. Once the needle 14 is inserted into an eye, the lever arm 40 can be repetitively depressed and released to cause the inner tube 54 to move cyclically within the needle 14 to thereby cut off portions of the vitreous that flow into the aperture 50. At the same time that the lever arm 40 is depressed to actuate the cutting action of the tube 54, the plug 34 is released from the orifice 30 so that a vacuum pressure is created by the action of the plunger 18 being urged out of the cavity 16 by spring 22. This action draws the small pieces of vitreous into the tube 54 where they will be eventually drawn into the cavity 32. When the physician has removed a sufficient quantity of the vitreous material, he can depress the lever 72 to allow the fluid from syringe 80 to flow through the tube 62 and into the opening formed within the eye by removal of the vitreous material. Typically, the physician is using visual observation to determine when a sufficient volume of vitreous material has been removed and also to determine when a sufficient quantity of fluid has been inserted to replace the vitreous material. However, the syringe 80 is also calibrated so that a measured quantity of drug or other fluid may be injected into the eye in the region in which the vitreous material has been removed.

Figure 3:
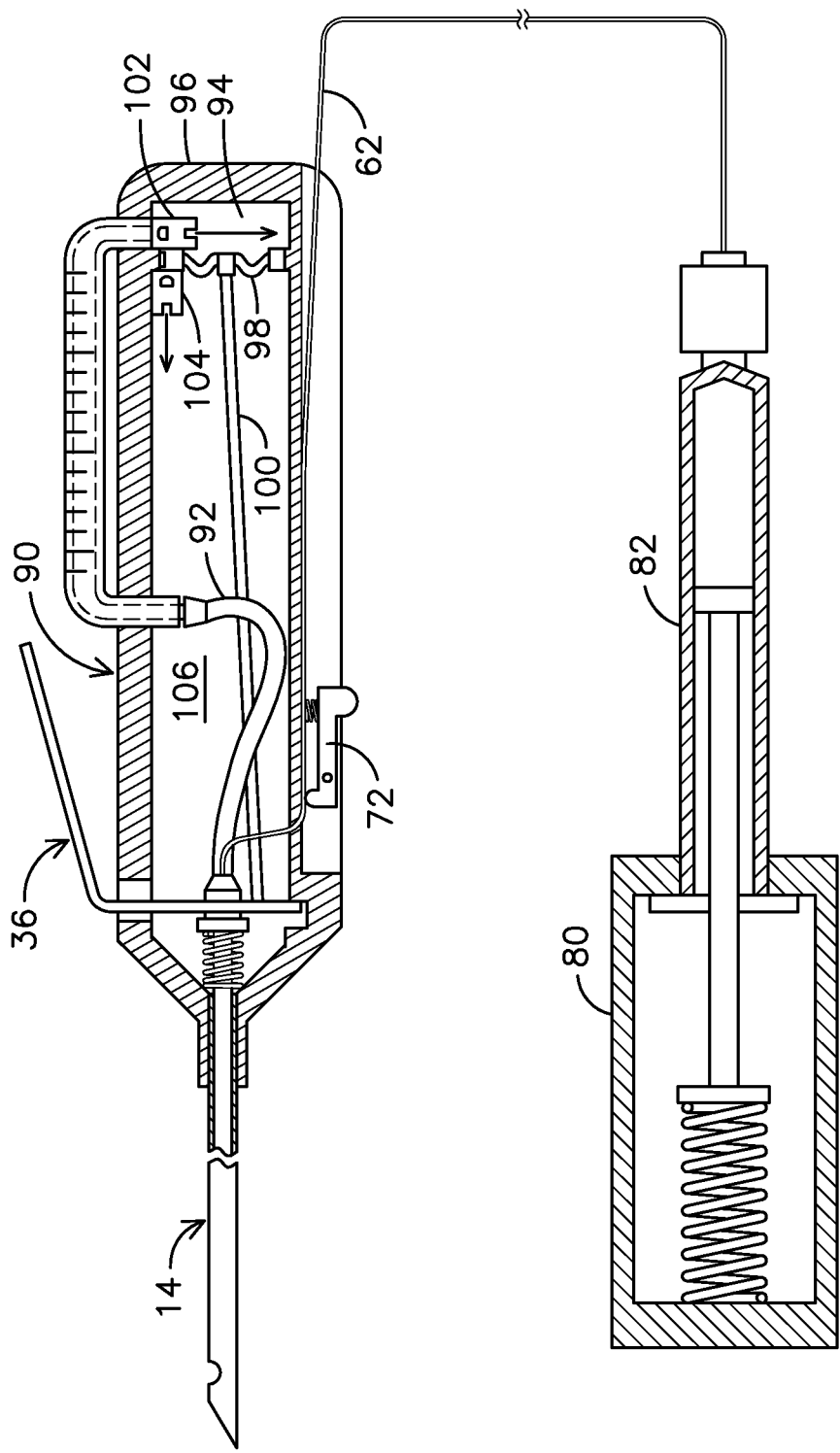
FIG. 3 is a cross-sectional drawing of another embodiment of the inventive injector-vitrector device.

FIG. 3 illustrates another embodiment of the present invention in which the suction action to remove vitreous fluid from the eye is obtained by mechanically cycling a membrane. Here, the needle portion 14 structure remains the same as in FIG. 1 but the main body portion is modified to create a closed housing 90. The pair of levers 36 and 72 are each mounted to the housing 90 similar to the structure of FIG. 1 and the tube 62 still connects to the external source of fluid at syringe 80 and the spring loaded mechanism 82. However, the tube 62 now passes into a suction tube 92 within housing 90. The suction tube 92 is connected at one end to the needle 14 so as to be able to create a vacuum or suction action within the needle. Another end of the tube 92 is connected to a secondary cavity 94 located within the housing 90. The cavity 94 is formed between a back end 96 of housing 90 and a flexible membrane 98.

A connecting rod 100 extends through housing 90 and connects at one end to about a center point of membrane 98. An opposite end of rod 100 is coupled to lever 36 such that pressing and releasing of lever arm 40 causes a reciprocating motion of rod 100 resulting in movement of membrane 98. As membrane 98 is pulled away from end wall 96, the fluid volume defined within the cavity 94 is increased. A one-way valve 102 allows fluid, air or liquid, to be drawn into cavity 94 via tube 92 as the membrane is pulled forward. When the lever 36 is released, the membrane moves toward rear wall 96 thereby decreasing the volume of cavity 94. A second one-way valve 104 provides a path for fluid to exit cavity 94 and be pushed into the large cavity 106 defined within housing 90. While the tube 92 is shown exiting the cavity 106 before being coupled to the cavity 94, it will be appreciated that different connections could be made to achieve the same result.

Figure 4A:
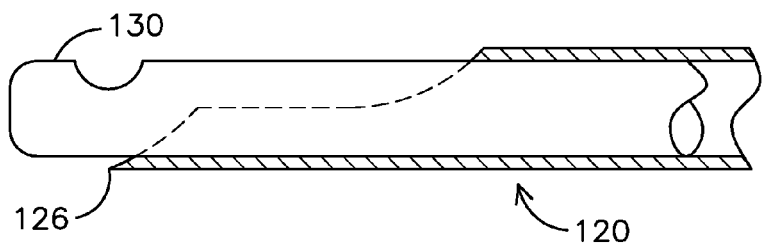
FIGS. 4a and 4b show an alternate embodiment of the probe tip for the intrector in which the sharpened tip is retracted once the probe has been inserted into an eye.
Figure 4B:
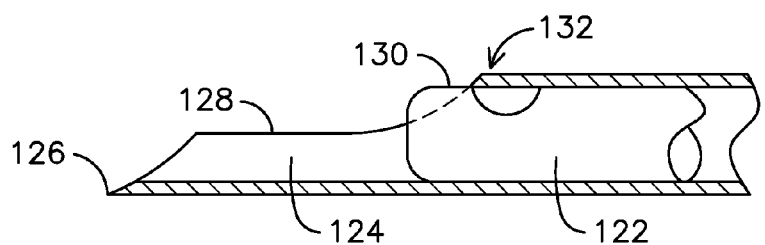

FIGS. 4a and 4b illustrate a variation of the sharp tip configuration described above and replaces the needle 14 with a probe 120 having an outer tube 124 and an inner tube/cutter 122. It can be realized in conjunction with or without the inner tube 46 used for transporting liquids and can be adapted to any commercially available vitreous cutter probe. The sharp end 48 of the needle 14 can be formed as a part of the telescopically retractable outer trocar tube 124 thereby providing the sharp cutter necessary to insert the probe into the vitreous cavity. Once the outer trocar tube 124 is retracted, the blunt tip 130 of the inner tube 122 of the cutter/probe allows safe operation in close proximity to the retina, without the risk of accidental injury due to the sharp tip. FIG. 4a shows the inner cutter tube 122 extended out past the outer trocar tube 124 so that the sharp tip 126 of the outer trocar tube 124 is not exposed. FIG. 4b shows the inner cutter tube 122 retracted within the outer trocar tube 124 so that the sharp tip 126 of the outer trocar tube 124 is exposed. This is the position that would be used initially to create an opening in the sclera to access the vitreous cavity. The cutting portion/tip 126 of the trocar tube 124 extends to approximately half of the tube circumference. The cutting edge 126 of the trocar tube ideally has the shape of a hypodermic bevel as is commonly found in devices such as hypodermic needles and trocars.

The cutting edge 126 creates an approximately half circular incision. The gradual ramp 128 extending from the cutting edge ensures that no further cutting of the incision occurs while the tip is advanced through the incision. The blunt tip 130 of the vitreous cutter/probe 122 is positioned in such a way relative to the outer trocar tube 124, that its distal end is protruding from the proximal edge 132 of the ramp. This ensures that the resulting tissue flap is displaced, rather than cut off by the proximal edge of the ramp. The combined length of the cutting edge and ramp of the trocar tube is approximately 1.5 to 3 mm.

Figure 5A:
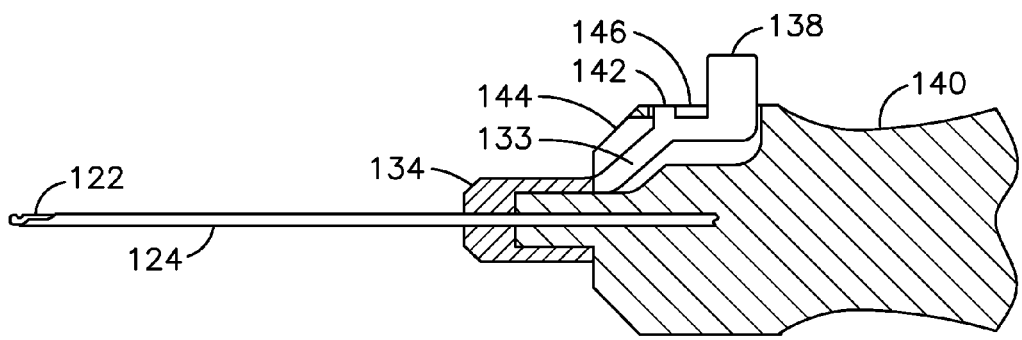
FIGS. 5a and 5b show one form for implementing the retractable probe tip.
Figure 5B:
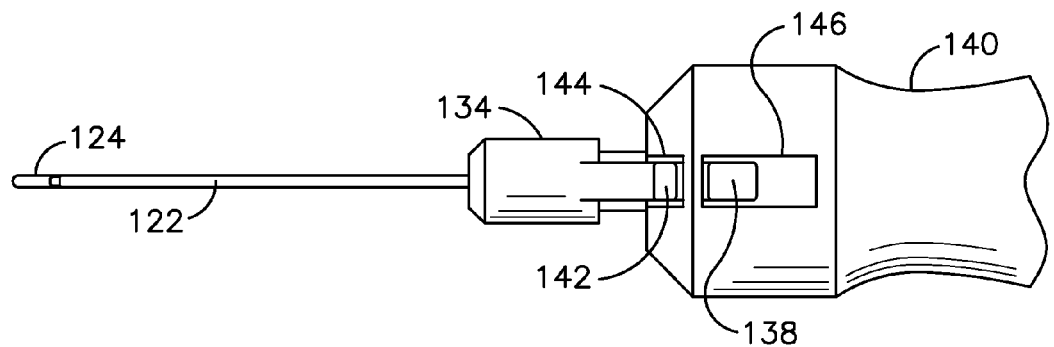

FIGS. 5a and 5b show one embodiment of a retraction mechanism for the telescoping outer trocar tube 124 to selectively expose and conceal the sharpened tip 126 for incisions. The cross-sectional view of FIG. 5a shows the outer trocar tube 124 in its retracted state concealing the sharpened tip 126 so that the blunt tip 130 of the inner tube/cutter projects out of the probe 120. The top view of FIG. 5b shows the outer trocar tube 124 in its extended state (extended out past the inner tube/cutter 122) exposing the sharpened tip 126 for incisions. The proximal end of the outer trocar tube 124 is secured in the cylindrical, telescopically movable hub 134 with its integral flexible and slidable member 133. The proximal end of the member 133 is shaped in the form of a button 138, which protrudes from the surface of the handpiece 140.

FIG. 5b shows a locking lug 142 engaged in a housing cutout 144, which secures the trocar tube 124 in its extended position during insertion of the device into the eye. Depressing the button 138 frees the locking lug 142 and enables the trocar tube 124 to be retracted into the position shown in FIG. 5a. The locking lug is now engaged in the proximal housing cutout 146.

Figure 6A:
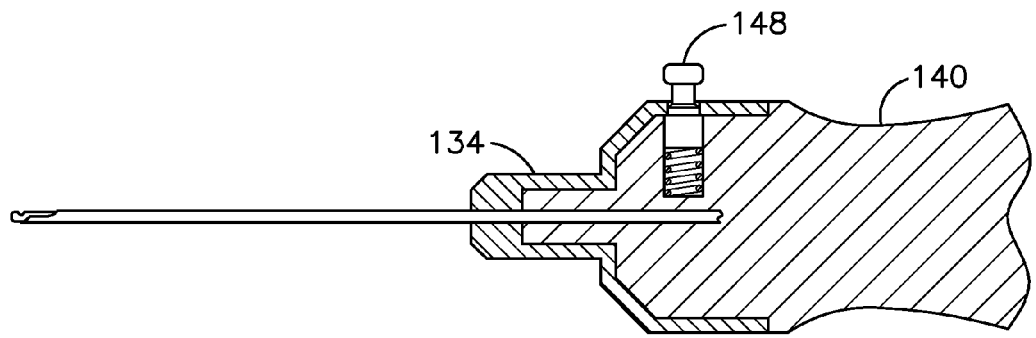
FIGS. 6a and 6b show another implementation of the retractable probe tip.
Figure 6B:
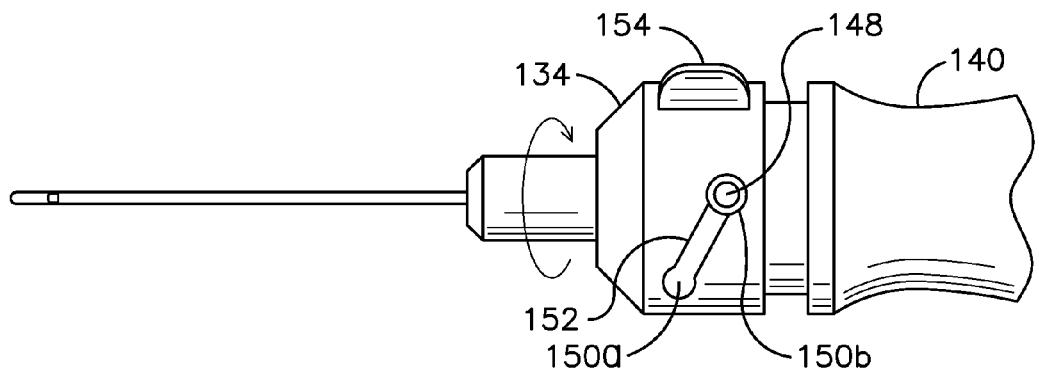

FIGS. 6a and 6b show another embodiment of the retraction mechanism of FIGS. 5a and 5b. The telescopically movable trocar hub 134 now extends well onto the handpiece and is secured in either end positions by a spring-loaded locking feature 148. The locking feature has two diameters: The larger diameter engages in either of the end position 150a or 150b of the housing cutout 152. Depressing the knob of the locking feature aligns the smaller diameter of the feature with the narrow portion of the housing cutout and allows the trocar hub 134 to be rotated between the two end positions. One or multiple tabs 154 located on the outside of the trocar hub may facilitate the manipulation.

The mechanism described in FIG. 6 can also be implemented with a simple axial, rather than the depicted rotational movement. Furthermore the same axial displacement could be achieved by using a threaded engagement between the trocar hub and the handpiece.

Further embodiments of a locking feature include crush bumps or tangs located in the housing cutout, which can engage a stationary dowel. Tangs, barbs or crush bumps may also be used between the trocar hub and handpiece to temporarily secure the device in either end position.

It will be appreciated that the present invention provides an advantageous way of removing small samples of vitreous material from an eye in order to provide space in the eye for injection of antibiotics or other drugs. Further, the device described herein can be constructed as a disposable device and provided as a pre-package sterile system. Still further, the device does not require any electrical connections and therefore simplifies the use such that it could be employed in non-operating room environment.

What is claimed is:
1. A probe for a vitrectomy tool comprising:
 a vitreous cutter tube having a blunt tip at a distal end and adapted to be coupled at a proximal end to a handpiece of a vitrectomy tool, wherein the vitreous cutter tube comprises an aperture extending into a central bore adapted to receive a flow of vitreous material;
 a reciprocal cutter fitted in the central bore of the vitreous cutter tube, the reciprocal cutter having a cutting edge adapted for travel across the aperture;
 a retractable outer trocar tube surrounding the vitreous cutter tube having an open distal end with a sharpened edge forming a bevel and a sharp tip;
 a retraction mechanism comprising a movable hub coupled to a proximal end of the outer trocar tube that imparts relative movement to the outer trocar tube for selectively extending and retracting the outer trocar tube between a first extended position wherein the sharp tip of the outer trocar is extended beyond the blunt tip of the vitreous cutter tube until the blunt tip remains partially protruding from a proximal end of the bevel to facilitate insertion into the eye without further cutting by the proximal end of the bevel and a second retracted position wherein the sharp tip of the outer trocar is retracted behind the blunt tip of the vitreous cutter tube to facilitate safe operation of the probe; wherein the retraction mecha- nism is configured to secure the outer trocar tube in the first extended position and in the second retracted position.

2. The probe of claim 1 wherein the retraction mechanism comprises a slidable member extending through the handpiece and protruding out therefrom as an activation member, wherein the slidable member imparts movement to the movable hub when activated by the activation member to selectively extend and retract the outer trocar tube between the first extended position and the second retracted position.

3. The probe of claim 2 wherein the slidable member further comprises a selectively releasable locking mechanism activated by the activation member to secure the outer trocar tube in the first extended position and the second retracted position.

4. The probe of claim 1 wherein the retraction mechanism comprises a mechanism adapted to be manipulated between two positions in a housing cutout, wherein the mechanism imparts movement to the movable hub when manipulated to selectively extend and retract the outer trocar tube in the first extended position and the second retracted position.

5. The probe of claim 4 wherein the mechanism comprises a spring-loaded locking mechanism adapted to be selectively manipulated between the two positions in the housing cutout and to provide axial or rotational movement to the hub.

6. The probe of claim 1 wherein the bevel further comprises a gradual ramp edge having a distal end starting from the sharp tip and extending approximately half of the circumference of the trocar to a proximal end of the ramp edge to create a half-circular incision when inserted into the eye.

7. The probe of claim 6 wherein the blunt tip of the vitreous cutter tube protrudes from the proximal end of the gradual ramp when the outer trocar tube is in the second retracted position adapted to ensure no further cutting of the incision occurs and the resulting tissue flap is displaced rather than cut off by the proximal end of the gradual ramp.

8. A vitrectomy tool for removing vitreous material from and injecting fluid into an eye of a patient comprising:
a housing body having a proximal end and a distal end;
a probe coupled to the proximal end of the housing body, wherein the probe comprises:
a vitreous cutter tube having a blunt tip at a distal end and adapted to be coupled at a proximal end to the housing, wherein the vitreous cutter tube comprises an aperture extending into a central bore adapted to receive a flow of vitreous material;
a reciprocal cutter fitted in the central bore of the vitreous cutter tube, the reciprocal cutter having a cutting edge adapted for travel across the aperture;
a retractable outer trocar tube surrounding the vitreous cutter tube having an open distal end with a sharpened edge forming a bevel and a sharp tip; and a retraction mechanism comprising a movable hub coupled to a proximal end of the outer trocar tube that imparts relative movement to the outer trocar tube for selectively extending and retracting the outer trocar tube between a first extended position wherein the sharp tip of the outer trocar is extended beyond the blunt tip of the vitreous cutter tube until the blunt tip remains partially protruding from a proximal end of the bevel to facilitate insertion into the eye without further cutting by the proximal end of the bevel and a second retracted position wherein the sharp tip of the outer trocar is retracted behind the blunt tip of the vitreous cutter tube to facilitate safe operation of the probe; wherein the retraction mechanism is configured to secure the outer trocar tube in the first extended position and in the second retracted position.

9. The vitrectomy tool of claim 8 wherein the retraction mechanism comprises a slidable member extending through the housing and protruding out therefrom as an activation member, wherein the slidable member imparts movement to the movable hub when activated by the activation member to selectively extend and retract the outer trocar tube in the first extended position and the second retracted position.

10. The vitrectomy tool of claim 9 wherein the slidable member further comprises a selectively releasable locking mechanism activated by the activation member to secure the outer trocar tube in the first extended position and the second retracted position.

11. The vitrectomy tool of claim 8 wherein the retraction mechanism comprises a mechanism adapted to be manipulated between two positions in a housing cutout, wherein the mechanism imparts movement to the movable hub when manipulated to selectively extend and retract the outer trocar tube in the first extended position and the second retracted position.

12. The vitrectomy tool of claim 11 wherein the mechanism comprises a spring-loaded locking mechanism adapted to be selectively manipulated between the two positions in the housing cutout and to provide axial or rotational movement to the hub.

13. The vitrectomy tool of claim 8 wherein the bevel further comprises a gradual ramp edge having a distal end starting from the sharp tip and extending approximately half of the circumference of the trocar to a proximal end of the ramp edge to create a half-circular incision when inserted into the eye.

14. The vitrectomy tool of claim 13 wherein the blunt tip of the vitreous cutter tube protrudes from the proximal end of the gradual ramp when the outer trocar tube is in the second retracted position adapted to ensure no further cutting of the incision occurs and the resulting tissue flap is displaced rather than cut off by the proximal end of the gradual ramp.

15. The vitrectomy tool of claim 8 further comprising a manually actuated lever adapted to drive the cutting edge of the reciprocal cutter across the aperture.

16. The vitrectomy tool of claim 8 further comprising an electrically powered actuator adapted to drive the cutting edge of the reciprocal cutter across the aperture.

17. The vitrectomy tool of claim 8 wherein the housing body comprises a cavity for receiving the flow of vitreous material from the vitreous cutter tube.

18. The vitrectomy tool of claim 8 further comprising a device for providing a source of fluid for injecting into an eye of the patient after removing vitreous material, the device connected to the vitrectomy tool via a transfer tube.

* * * * *